United States Patent [19]
Nishikawa

[11] Patent Number: 6,153,766
[45] Date of Patent: *Nov. 28, 2000

[54] METHOD OF PRODUCING 4-HYDROXY-2-PYRROLIDINONE AND METHOD OF PURIFYING THE SAME

[75] Inventor: Masahiro Nishikawa, Niigata, Japan

[73] Assignee: Daicel Chemical Industries, Ltd., Osaka, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/979,444

[22] Filed: Nov. 25, 1997

[30] Foreign Application Priority Data

Nov. 26, 1996 [JP] Japan ..................................... 8-314924

[51] Int. Cl.$^7$ .................... C07D 207/12; C07D 207/267; C07D 207/06
[52] U.S. Cl. ........................... 548/544; 548/554; 548/579
[58] Field of Search ................................... 548/544, 579, 548/554

[56] References Cited

U.S. PATENT DOCUMENTS 4,003,911  1/1977  Scribner et al. ..................... 260/326.2

FOREIGN PATENT DOCUMENTS

| 0 787 718 A1 | 8/1997 | European Pat. Off. . |
| 8-119935 | 5/1996 | Japan . |
| 2 008 110 | 5/1979 | United Kingdom . |
| 96/33603 | 5/1995 | WIPO . |
| WO96/36603 | 11/1996 | WIPO . |

OTHER PUBLICATIONS

Larcheveque et al., *Tetrahedron*, 46:4277–4282 (1990).
Pellegata et al., *Synthesis*, 614–616 (Aug. 1978).
Kobayaski et al., "Preparation of optically active 2–pyrrolidinones as intermediates for antibacterial carbapenems", Chemical Abstracts, 125:151, Aug. 26, 1996.

*Primary Examiner*—Joseph K. McKane
*Assistant Examiner*—Joseph Murray
*Attorney, Agent, or Firm*—Fish & Richardson P.C.

[57] ABSTRACT

4-Hydroxy-2-pyrrolidinone which is useful as a raw material of drugs can be produced rapidly and highly selectively in a high yield from an optically active or recemic 4-amino-3-hydroxybutylic acid derivative or a 4-azido-3-hydroxybutyric acid derivative by adding a base catalyst to the reaction system. 4-Hydroxy-2-pyrrolidinone having a high optical purity can be obtained by carrying out recrystallization of optically active 4-hydroxy-2-pyrrolidinone without using a poor solvent.

14 Claims, No Drawings

METHOD OF PRODUCING 4-HYDROXY-2-PYRROLIDINONE AND METHOD OF PURIFYING THE SAME

FIELD OF THE INVENTION

The present invention relates to a method of producing optically active or racemic 4-hydroxy-2-pyrrolidinone, which is useful as a raw material of drugs, and to a method of purifying optically active 4-hydroxy-2-pyrrolidinone.

BACKGROUND OF THE INVENTION

4-Amino-3-hydroxybutyric acid and its ester derivatives are synthetic intermediate important for the production of 4-hydroxy-2-pyrrolidinone. This compound is derived from 4-azido-3-hydroxybutyric acid or its ester derivatives through reduction or the other methods (Tetrahedron, 46, 4227 (1990), JP-A-Hei-8-119935, etc.).

However, the ring-closing reaction of a 4-amino-3-hydroxybutyric acid derivative to 4-hydroxy-2-pyrrolidinone requires an expensive condensation agent such as hexamethyldisilazane when 4-amino-3-hydroxybutyric acid is used as a starting material (Synthesis, 1978, P.614).

The ring-closing reaction of 4-amino-3-hydroxybutyric acid ester to 4-hydroxy-2-pyrrolidinone can be carried out by heating 4-amino-3-hydroxybutyric acid ester in a solvent such as alcohol. By only such heat treatment, the reaction takes long time since the reaction rate of the ring-closing reaction is low. Also, the isolated yield is reduced because of unreacted 4-amino-3-hydroxybutyric acid ester and the other by-products.

Further, 4-hydroxy-2-pyrrolidinone having a high optical purity cannot be obtained by recrystallization, in the case of 4-hydroxy-2-pyrrolidinone having a low optical purity derived from an optically active starting material having a low optical purity.

SUMMARY OF THE INVENTION

An object of the present invention is to solve the above problems so that the reaction for deriving 4-hydroxy-2-pyrrolidinone from an optically active or racemic 4-amino-3-hydroxybutyric acid derivative or a 4-azido-3-hydroxybutyric acid derivative can proceed rapidly and highly selectively to give a high yield. Another object of the present invention is to provide a method of purifying optically active 4-hydroxy-2-pyrrolidinone to give a high purity.

From the fact that a base functions to promote amidation of carboxylic acid ester (Course of New Experimental Chemistry, 14-II, p.1146 (Maruzen)), the present inventors assumed that, if such a base is used as a catalyst in the ring-closing reaction of 4-amino-3-hydroxybutyric acid ester derivative to 4-hydroxy-2-pyrrolidinone, the base functions catalyze intra-molecular amidation of the ester so that the ring-closing reaction can proceed rapidly and highly selectively to give a high yield. As a result of intensive investigation, the present inventors have found that the ring-closing reaction of 4-amino-3-hydroxybutyric acid ester to 4-hydroxy-2-pyrrolidinone can be promoted by adding a catalytic amount of a base to the reaction system, that the reaction can be completed for an extremely short period of time under heating or even without heating as in the conventional method, and that highly pure 4-hydroxy-2-pyrrolidinone can be obtained in a higher yield compared with the conventional method.

The present inventors have also found that, if a base catalyst is contained in the reaction system at the reaction stage just prior to the above conversion reaction, namely the stage that an azido group of 4-azido-3-hydroxybutyric acid ester is converted into an amino group by catalytic hydrogenation or the like, the base catalyst functions to catalyze intramolecular amidation of the ester without inhibiting the reduction reaction, the ring-closing of 4-amino-3-hydroxybutyric acid ester formed by the reduction occurs subsequently without heating or the like treatment to give 4-hydroxy-2-pyrrolidinone in one step.

Since 4-hydroxy-2-pyrrolidinone having a high optical purity could not be obtained by the conventional method when 4-hydroxy-2-pyrrolidinone having a low optical purity derived from an optically active starting material having a low optical purity is recrystallized, the present inventors further intensively studied to solve the problem. The inventors assumed that a poor solvent used for recrystallization in the conventional method can improve the yield in the recrystallization step but thereby lowering solubility of 4-hydroxy-2-pyrrolidinone, which results in additionally crystallizing an unnecessary antipode to reduce the optical purity of resulting 4-hydroxy-2-pyrrolidinone. On the above assumption, the inventors carried out recrystallization without using a poor solvent and have found that highly optically pure 4-hydroxy-2-pyrrolidinone can be obtained by this method.

The present invention relates to a method of producing 4-hydroxy-2-pyrrolidinone represented by the formula (2):

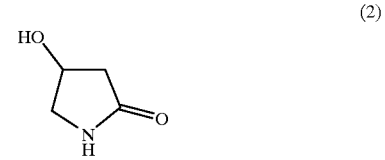

(2)

which comprises effecting the ring-closing reaction of 4-amino-3-hydroxybutyric acid ester represented by the formula (1):

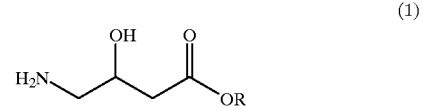

(1)

wherein R represents a lower alkyl group having 1 to 6 carbon atom(s) or a benzyl group, in the presence of a base catalyst.

The present invention also relates to a method of producing 4-hydroxy-2-pyrrolidinone represented by the formula (2):

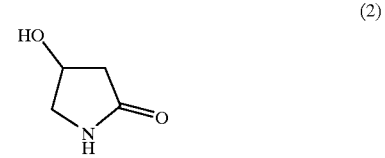

(2)

which comprises adding a base catalyst to 4-azido-3-hydroxybutyric acid ester represented by the formula (3):

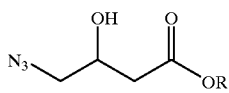

(3)

wherein R represents a lower alkyl group having 1 to 6 carbon atom(s) or a benzyl group and effecting catalytic hydrogenation in the presence of a metal catalyst.

The present invention further relates to a method of purifying 4-hydroxy-2-pyrrolidinone which comprises recrystallizing optically active 4-hydroxy-2-pyrrolidinone in the absence of a poor solvent.

DETAILED DESCRIPTION OF THE INVENTION

The term "poor solvent" used in the present invention means a solvent in which 4-hydroxy-2-pyrrolidinone cannot be dissolved at a room temperature or under heating, including ethyl acetate, diethyl ether, diisopropyl ether, methyl t-butyl ether, benzene, toluene, pentane, hexane, cyclohexane, and the like.

4-Amino-3-hydroxybutyric acid ester represented by the formula (1) according to the present invention can be obtained by esterification of 4-amino-3-hydroxybutyric acid, reduction of 4-azido-3-hydroxybutyric acid ester, or the like. Alternatively, 4-azido-3-hydroxybutyric acid ester can be obtained by reacting 4-halo-3-hydroxybutyric acid ester with sodium azide (Tetrahedron, 46, 4227 (1990), JP-A-Hei-8-119935, etc.). In the formula (1), an ester group represented by R includes a lower alkyl group having 1 to 6 carbon atom(s) such as a methyl group, an ethyl group, a propyl group, an isopropyl group, or a butyl group, a benzyl group, or the like.

4-Hydroxy-2-pyrrolidinone represented by the formula (2) according to the present invention can be obtained by the ring-closing reaction of 4-amino-3-hydroxybutyric acid ester represented by the formula (1).

The ring-closing reaction of 4-amino-3-hydroxybutyric acid ester represented by the formula (1) in which the hydroxyl group at the 3-position is in R- or S-configuration or racemic modification of 4-amino-3-hydroxybutyric acid ester can be carried out in a solvent or without a solvent, preferably in a solvent. Though the solvent to be used is not particularly limited, examples thereof include alcohols such as methanol, ethanol, 1-propanol, 2-propanol, or the like, ethers such as tetrahydrofuran, 1,4-dioxane, or the like, esters such as ethyl acetate or the like, and amides such as dimethylformamide or the like. It is preferable to use lower alcohols such as methanol, ethanol, 1-propanol, 2-propanol, or the like, with methanol being particularly preferred.

The ring-closing reaction can proceed rapidly and highly selectively to give a high yield by adding a base catalyst to the reaction system. The base catalyst used herein include, for example, inorganic bases such as sodium hydroxide, potassium hydroxide, sodium carbonate, potassium carbonate, sodium hydrogencarbonate, sodium acetate, ammonium acetate, or the like, metal alkoxides such as sodium methoxide, sodium ethoxide, or the like, amines such as triethylamine, diisopropylethylamine, or the like. It is preferable to use that soluble in the reaction solvent including amines or metal alkoxides. Particularly preferred are metal alkoxides such as sodium methoxide, sodium ethoxide, or the like. The base catalyst is usually used in an amount of 0.1 to 25%, preferably 0.1 to 10%, more preferably 0.5 to 5%, in terms of a molar ratio to 4-amino-3-hydroxybutyric acid ester. The reaction temperature ranges usually from 0° C. to a reflux temperature of the solvent used, preferably from room temperature to 70° C. Though the reaction time varies depending on the reaction temperature, it ranges usually from 1 to 4 hours when the reaction temperature ranges from room temperature to about 35° C., and it ranges usually from 10 minutes to 1 hour when the reaction temperature is from 35 to 70° C. or higher. In this respect, the present invention is quite different from the conventional method (JP-A-Hei-8-119935) in which the reaction time is 4 to 6 hours when the reaction temperature is from 50 to 70° C.

When the reaction solvent is an alcohol and an alkyl group of the alcohol does not correspond to an ester group of 4-amino-3-hydroxybutyric acid ester used as a starting material, transesterification may sometimes occur prior to the ring-closing reaction. If the ring-closing reaction of 4-amino-3-hydroxybutyric acid ester is carried out in methanol in the absence of a base catalyst, the reaction rate and the yield are lower than those in the case that the base catalyst is used. From this fact, it is clear that the ring-closing reaction-promoting effect of the present invention is not exerted only by, for example, transesterification in which an ester group of 4-amino-3-hydroxybutyric acid ester is replaced with a lower alkyl group which is more reactive in the amidation reaction (for example, ethyl ester is converted into methyl ester in methanol.).

According to the present invention, catalytic hydrogenation of 4-azido-3-hydroxybutyric acid ester represented by the formula (3) in which the hydroxyl group at the 3-position is in R- or S-configufation or racemic modification of 4-azido-3-hydroxybutyric acid ester and the subsequent ring-closing reaction are accomplished in one step by adding a base catalyst to the catalytic hydrogenation reaction system. The ester group represented by R in the formula (3) is exemplified by, for example, a lower alkyl group having 1 to 6 carbon atom(s), such as a methyl group, an ethyl group, a propyl group, an isopropyl group, a butyl group, or the like, or a benzyl group. The catalytic hydrogenation and subsequent ring-closing reactions are usually carried out in a solvent including alcohols such as methanol, ethanol, 1-propanol, 2-propanol, or the like, ethers such as tetrahydrofuran, 1,4-dioxane, or the like, esters such as ethyl acetate or the like, and amides such as dimethylformamide or the like. Among these, lower alcohols such as methanol, ethanol, 1-propanol, 2-propanol, or the like are preferred, with methanol being particularly preferred.

As the metal catalyst used in catalytic hydrogenation, those usually used for reduction of an azide compound, including palladium, platinum, nickel, and the like, can be used. These catalysts may be metal itself or those carried by active carbon and the like. Preferably, 5 to 10% palladium-carbon catalyst and 3 to 5% platinum-carbon catalyst can be used. Particularly, 5 to 10% palladium-carbon catalyst is preferred. The metal catalyst is used in an amount ranging from usually 0.5 to 50 wt %, preferably 0.5 to 20 wt %, particularly preferably 1 to 10 wt %, based on the weight of 4-azido-3-hydroxybutyric acid ester.

Examples of the base catalyst to be used include inorganic bases such as sodium hydroxide, potassium hydroxide, sodium carbonate, potassium carbonate, sodium hydrogencarbonate, sodium acetate, ammonium acetate, or the like, metal alkoxides such as sodium methoxide, sodium ethoxide, or the like, amines such as triethylamine, diisopropylethylamine, or the like. It is preferable to use that soluble in the reaction solvent including amines or metal alkoxides. Particularly preferred are metal alkoxides such as sodium methoxide, sodium ethoxide, or the like. The base catalyst is usually used in an amount of 0.1 to 25%, preferably 0.1 to 10%, more preferably 0.5 to 5%, in terms of a molar ratio to 4-amino-3-hydroxybutyric acid ester.

The reaction can be carried out under the above conditions and under stirring in hydrogen gas atmosphere. The ring-closing of 4-amino-3-hydroxybutyric acid ester formed by reduction of 4-azido-3-hydroxybutyric acid ester is subsequently effected to give 4-hydroxy-2-pyrrolidinone. The reaction temperature is determined arbitrarily within the range usually from 0° C. to the reflux temperature of the solvent used. The reaction time usually ranges from 30 minutes to 6 hours.

After completion of the above ring-closing reaction, the reaction solvent is distilled off if necessary and recrystallization is carried out to isolate 4-hydroxy-2-pyrrolidinone of a high purity whose configuration corresponds to that of the starting material. A solvent used for recrystallization may be arbitrarily selected from those in which 4-hydroxy-2-pyrrolidinone can dissolve. It is preferably to use alcohols such as methanol, ethanol, 1-propanol, 2-propanol, 1-butanol, or the like or nitrites such as acetonitrile or the like in view of superiority in solubility, the purification effect, the yield of crystals, and the like. These solvents are used alone or in a mixture thereof in an arbitrary mixing ratio.

Particularly, upon recrystallization of optically active 4-hydroxy-2-pyrrolidinone, an optical purity of resulting 4-hydroxy-2-pyrrolidinone can be considerably improved by using ethanol or the like solvent in place of a poor solvent. For example, 4-hydroxy-2-pyrrolidinone having an optical purity of about 80% ee can be improved up to 99% ee or higher by recrystallization. Further, highly optically pure 4-hydroxy-2-pyrrolidinone can be obtained from one having a low optical purity if recrystallization is repeatedly carried out.

According to the present invention, 4-hydroxy-2-pyrrolidinone that is useful as an intermediate for producing a drug and the like can be produced rapidly in a high yield. In the case of an optically active compound, 4-hydroxy-2-pyrrolidinone having a high optical purity can be obtained.

The following examples will demonstrate the present invention in more detail, but are not to be construed to limit the scope of the present invention.

EXAMPLE 1

Production of (S)-4-hydroxy-2-pyrrolidinone

Ethyl (S)-4-azido-3-hydroxybutyrate (2.88 g, 16.6 mmol) was dissolved in methanol (30 ml), 5% palladium-carbon catalyst (130 mg) was added thereto, and the mixture was stirred at room temperature for 2 hours with blowing hydrogen gas. After completion of catalytic hydrogenation, the catalyst was filtered off and a 28% methanol solution of sodium methoxide (60 mg, 0.3 mmol as NaOMe) was added to the resulting ethyl (S)-4-amino-2-hydroxybutyrate solution. The mixture was subjected to reflux under heating for 15 minutes. After completion of the ring-closing reaction, methanol was distilled off under reduced pressure and the resulting crude crystals were recrystallized from ethanol (10 ml) to obtain colorless crystals.

Yield: 1.40 g (83.4%).
Melting point: 156.2–157.6° C.

NMR (500 MHz. $D_2O$, δ ppm): 4.62 (1H, m), 3.72 (1H, dd, J=5.4 11.7 Hz), 3.33 (1H, dd, J=1.3 11.7 Hz), 2.77 (1H, dd, J=6.4 17.7 Hz), 2.27 (1H, dd, J=1.9 17.7 Hz).
$[\alpha]D25$ −58.5° (c=1.01, $H_2O$).
IR (KBr, $cm^{-1}$): 3242, 3135, 1674, 1303, 968, 682.

(R)-4-hydroxy-2-pyrrolidinone was not detected as a result of the optical purity analysis by HPLC using an optical resolution column (column: CHIRALPAK AD, eluent: hexane/ethanol/methanol/TFA=95/5/2/0.1).

EXAMPLE 2

Production of (S)-4-hydroxy-2-pyrrolidinone

A 28% methanol solution of sodium methoxide (40 mg, 0.2 mmol as NaOMe) was added to a methanol solution (25 ml) of ethyl (S)-4-amino-2-hydroxybutyrate (1.32 g, 9.0 mmol) and the mixture was stirred at room temperature for 2 hours. After completion of the ring-closing reaction, methanol was distilled off under reduced pressure and the resulting crude crystals were recrystallized from ethanol to obtain colorless crystals. The yield was 0.71 g (79%) and the melting point was 156.6–157.9° C.

The NMR data, IR data, and behavior during the HPLC analysis using an optical resolution column of the thus-obtained colorless crystals were identical with those obtained in Example 1.

EXAMPLE 3

Production of (S)-4-hydroxy-2-pyrrolidinone

Ethyl (S)-4-azido-3-hydroxybutyrate (4.8 g, 27.7 mmol) was dissolved in methanol (50 ml) and 5% palladium-carbon catalyst (100 mg) and a 28% methanol solution of sodium methoxide (280 mg, 1.4 mmol as NaOMe) were added thereto. The mixture was stirred at room temperature for 2.5 hours with blowing hydrogen gas to effect reduction and subsequent ring-closing reactions. The catalyst was filtered off and the filtrate was concentrated under reduced pressure. The resulting crude crystals were recrystallized from ethanol (17 ml) to obtain colorless crystals. The yield was 2.1 g (76%) and the melting point was 156.7–157.6° C.

The NMR data, IR data, and behavior during the HPLC analysis using an optical resolution column of the thus-obtained colorless crystals were identical with those obtained in Example 1.

EXAMPLE 4

Recrystallization of (S)-4-hydroxy-2-pyrrolidinone (S)-4-hydroxy-2-pyrrolidinone (1.5 g. 14.8 mmol) having an optical purity of 80% ee was dissolved in ethanol (10 ml) under heating. After cooling the solution, the precipitated crystals were collected by filtration and washed with cold ethanol to obtain colorless crystals. The yield was 1.15 g (77%).

As a result of the optical purity analysis by HPLC using CHIRALPAK AD, the optical purity of the crystals was 99.2% ee. The melting point was 154.8–156.4° C.

When (S)-4-hydroxy-2-pyrrolidinone having an optical purity of 95% ee was recrystallized in the same manner as above, (R)-4-hydroxy-2-pyrrolidinone was not detected by the HPLC analysis of the obtained crystals. The melting point was 156.7–157.6° C.

Reference Example 1

Production of (S)-4-hydroxy-2-pyrrolidinone without Adding a Base Catalyst

Methyl (S)-4-azido-3-hydroxybutyrate (2.64 g, 16.6 mmol) was dissolved in methanol (30 ml) and 5% palladium-carbon catalyst (150 mg) was added. The mixture was stirred at room temperature for 2 hours with blowing hydrogen gas. When the catalytic hydrogenation reaction was completed, ring-closed 4-hydroxy-2-pyrrolidinone was not observed. In other words, when a base catalyst was not used, 4-hydroxy-2-pyrrolidinone was not synthesized in one step. The catalyst was filtered off and the thus-obtained methanol solution of methyl (S)-4-amino-2-hydroxybutyrate was subjected to reflux under heating for 4.5 hours. Methanol was distilled off under reduced pressure and the resulting crude crystals were recrystallized from ethanol (8 ml) to obtain colorless crystals. The yield of the colorless crystals was lower than that obtained in the case of using a base catalyst. The yield was 1.05 g (62.5%).

Reference Example 2

Production of (R)-4-hydroxy-2-pyrrolidinone without Adding a Base Catalyst

An ethanol solution (50 ml) of ethyl (R)-4-amino-3-hydroxybutyrate (4.4 g, 30 mmol) was subjected to reflux under heating for 12 hours. Ethanol was distilled off and the thus-obtained crude crystals were recrystallized from ethanol (14 ml) to obtain pale yellow crystals. Notwithstanding the heat treatment for a long time, the yield was lower than that obtained in the case of using a base catalyst. The yield was 2.0 g (67%).

Reference Example 3

Recrystallization of (S)-4-hydroxy-2-pyrrolidinone (S)-4-hydroxy-2-pyrrolidinone (1.5 g, 14.8 mmol) having an optical purity of 80% ee was dissolved in ethanol (10 ml) under heating and ethyl acetate (20 ml) was added thereto followed by cooling. The precipitated crystals were collected by filtration and washed with ethanol-ethyl acetate to obtain crystals (conventional method). The yield was 1.24 g (83%).

As a result of the optical purity analysis by HPLC using CHIRALPAK AD, the optical purity of the resulting crystals was 92.8% ee.

When recrystallization was carried out from only ethanol (10 ml) without adding ethyl acetate (Example 4), the yield was 77% but the optical purity was remarkably increased to 99.2%. Namely, when recrystallization is carried out using a poor solvent such as ethyl acetate, the yield is improved compared with that obtained by recrystalization from only ethanol, but its optical purity which is particularly important to isolate an optically active compound is decreased.

What is claimed is:

1. A method of producing 4-hydroxy-2-pyrrolidinone represented by the formula (2):

(2)

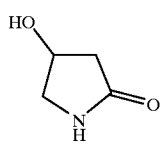

which comprises (a) using a metal catalyst to promote a catalytic hydrogenation reaction of 4-azido-3-hydroxybutyric acid ester represented by the formula (3):

(3)

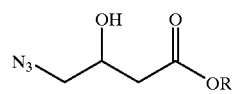

wherein R represents a lower alkyl group having 1 to 6 carbon atom(s) or a benzyl group, and (b) catalyzing a ring-closing reaction with a base catalyst selected from the group consisting of inorganic bases, metal alkoxides, and amines; the catalytic hydrogenation reaction and the ring-closing reaction being carried out without isolation of an intermediate.

2. The method of claim 1, wherein the molar ratio of said base catalyst to the 4-azido-3-hydroxybutyric acid ester is between 1:1,000 to 1:4.

3. The method of claim 1, wherein the reactions are carried out in a solvent selected from the group consisting of alcohols, ethers, esters, and amides.

4. The method of claim 1, wherein said metal catalyst is selected from the group consisting of palladium, platinum, nickel, and those carried by active carbon.

5. The method of claim 1, wherein the ratio of said metal catalyst to the 4-azido-3-hydroxybutyric acid ester is between 1:200 to 1:2 by weight.

6. The method of claim 1, wherein the base catalyst is an alkali metal alkoxide.

7. The method of claim 2, wherein the molar ratio of the base catalyst to the 4-azido-3-hydroxybutyric acid ester is between 1:200 to 1:20.

8. The method of claim 3, wherein the solvent is methanol.

9. The method of claim 5, wherein the ratio of the metal catalyst to the 4-azido-3-hydroxybutyric acid ester is between 1:100 to 1:10 by weight.

10. The method of claim 1, wherein said base catalyst is a metal alkoxide.

11. The method of claim 1, wherein said base catalyst is an amine.

12. The method of claim 1, wherein the molar ratio of the base catalyst to the 4-azido-3-hydroxybutyric acid ester is between 1:1,000 to 1:10.

13. The method of claim 5, wherein the ratio of the metal catalyst to the 4-azido-3-hydroxybutyric acid ester is between 1:200 to 1:5 by weight.

14. The method of claim 1, wherein the reactions are carried out in a $C_{1-3}$ alcohol.

* * * * *